United States Patent
Serov et al.

(10) Patent No.: US 9,425,464 B2
(45) Date of Patent: Aug. 23, 2016

(54) CARBENDAZIM-BASED CATALYTIC MATERIALS

(71) Applicants: Alexey Serov, Albuquerque, NM (US); Plamen B Atanassov, Santa Fe, NM (US)

(72) Inventors: Alexey Serov, Albuquerque, NM (US); Plamen B Atanassov, Santa Fe, NM (US)

(73) Assignee: STC.UNM, Albuquerque, NM (US)

( * ) Notice: Subject to any disclaimer, the term of this patent is extended or adjusted under 35 U.S.C. 154(b) by 0 days.

(21) Appl. No.: 14/414,132

(22) PCT Filed: Jul. 11, 2013

(86) PCT No.: PCT/US2013/050006
§ 371 (c)(1),
(2) Date: Jan. 12, 2015

(87) PCT Pub. No.: WO2014/011831
PCT Pub. Date: Jan. 16, 2014

(65) Prior Publication Data
US 2015/0228985 A1    Aug. 13, 2015

Related U.S. Application Data

(60) Provisional application No. 61/670,216, filed on Jul. 11, 2012.

(51) Int. Cl.
| | |
|---|---|
| B01J 23/745 | (2006.01) |
| C07D 235/30 | (2006.01) |
| H01M 4/90 | (2006.01) |
| C07D 235/32 | (2006.01) |

(Continued)

(52) U.S. Cl.
CPC ............ H01M 4/9075 (2013.01); B01J 23/745 (2013.01); C07D 235/30 (2013.01); C07D 235/32 (2013.01); H01M 4/90 (2013.01); H01M 4/9041 (2013.01); B01J 37/084 (2013.01); H01M 2008/1095 (2013.01); Y02E 60/50 (2013.01)

(58) Field of Classification Search
CPC  B01J 20/3057; B01J 2229/40; B01J 23/745; B01J 37/084; C07D 235/30; C07D 235/32
USPC ................................ 502/155, 167; 977/783
See application file for complete search history.

(56) References Cited

U.S. PATENT DOCUMENTS

| | | | |
|---|---|---|---|
| 7,678,728 B2 | 3/2010 | Olson et al. | |
| 2005/0079374 A1 | 4/2005 | Asai et al. | |

(Continued)

FOREIGN PATENT DOCUMENTS

| | | | | |
|---|---|---|---|---|
| JP | 2004-342337 | * 12/2004 | ............... | H01M 4/88 |
| KR | 10-2012-0052483 | * 5/2012 | ............... | C01B 31/02 |
| WO | 2012/009467 | * 1/2012 | ............... | B01J 23/46 |

OTHER PUBLICATIONS

"Templated non-PGM cathode catalysts derived from iron and poly(ethyleneimine) precursors," Alexey Serov et al. Applied Catalysis B: Environmental 127 (2012), pp. 300-306.*

(Continued)

*Primary Examiner* — Patricia L Hailey
(74) *Attorney, Agent, or Firm* — Gonzales Patent Services; Ellen M. Gonzales

(57) ABSTRACT

A method of preparation of M-N—C catalytic material utilizing a sacrificial support approach and using inexpensive and readily available metal precursors and carbendazim (CBDZ) as the carbon source is described.

20 Claims, 9 Drawing Sheets

(51) Int. Cl.
*B01J 37/08* (2006.01)
*H01M 8/10* (2016.01)

(56) References Cited

U.S. PATENT DOCUMENTS

| 2006/0263288 A1* | 11/2006 | Pak ..................... B01J 21/18 423/445 R |
| 2010/0167106 A1 | 7/2010 | Pak et al. |
| 2011/0287174 A1 | 11/2011 | Calabrese Barton et al. |
| 2012/0219735 A1 | 8/2012 | Bakkar |

OTHER PUBLICATIONS

"Original Mechanochemical Synthesis of Non-Platinum Group Metals Oxygen Reduction Reaction Catalysts Assisted by Sacrificial Support Method," Alexey Serov et al. Electrochimica Acta 179 (2015), pp. 154-160.*

"Nano-structured non-platinum catalysts for automotive fuel cell application," Alexey Serov et al. Nano Energy (2015), 16, pp. 293-300.*

Garsuch et al., Fuel Cell Studies on a Non-Noble Metal Catalyst Prepared by a Template Assisted Synthesis Route Journal of the Electrochemical Society, vol. 155, No. 9 Jul. 18, 2008.

Jaouen et al., Recent advances in non-precious metal catalysis for oxygen-reduction reaction in polymer electrolyte fuel cells, Energy & Environmental Science, vol. 4 pp. 114-130, Oct. 18, 2010.

Atanassov et al Non-platinum Electrocatalysts for Polymer Electrolyte Fuel Cells, The Electrochemical Society, Inc., 205th Meeting, Abs. 205, 2004.

* cited by examiner

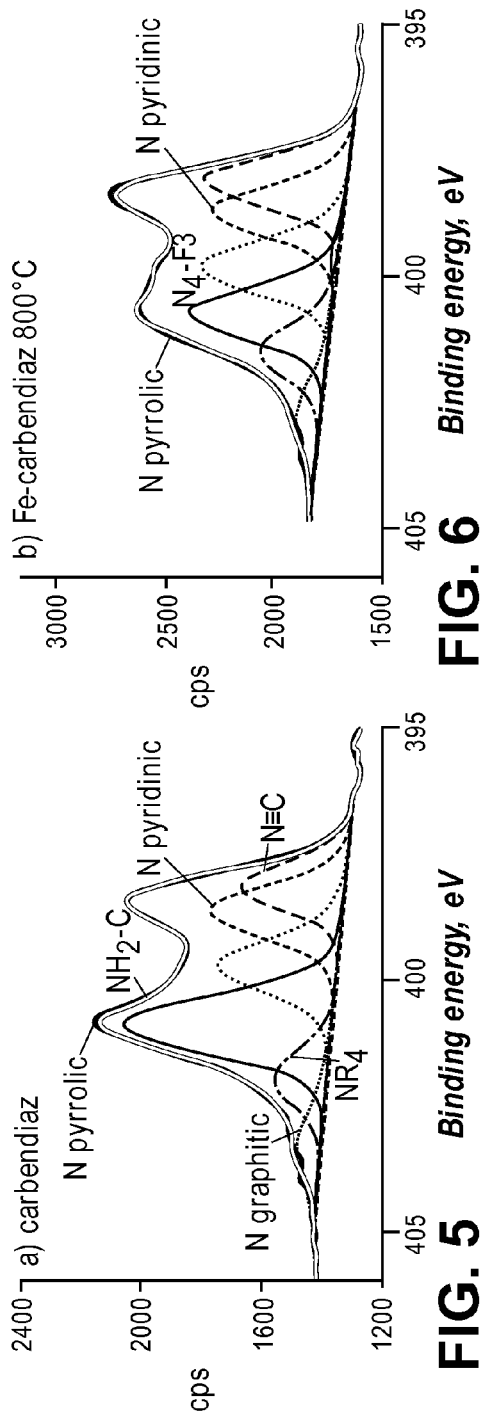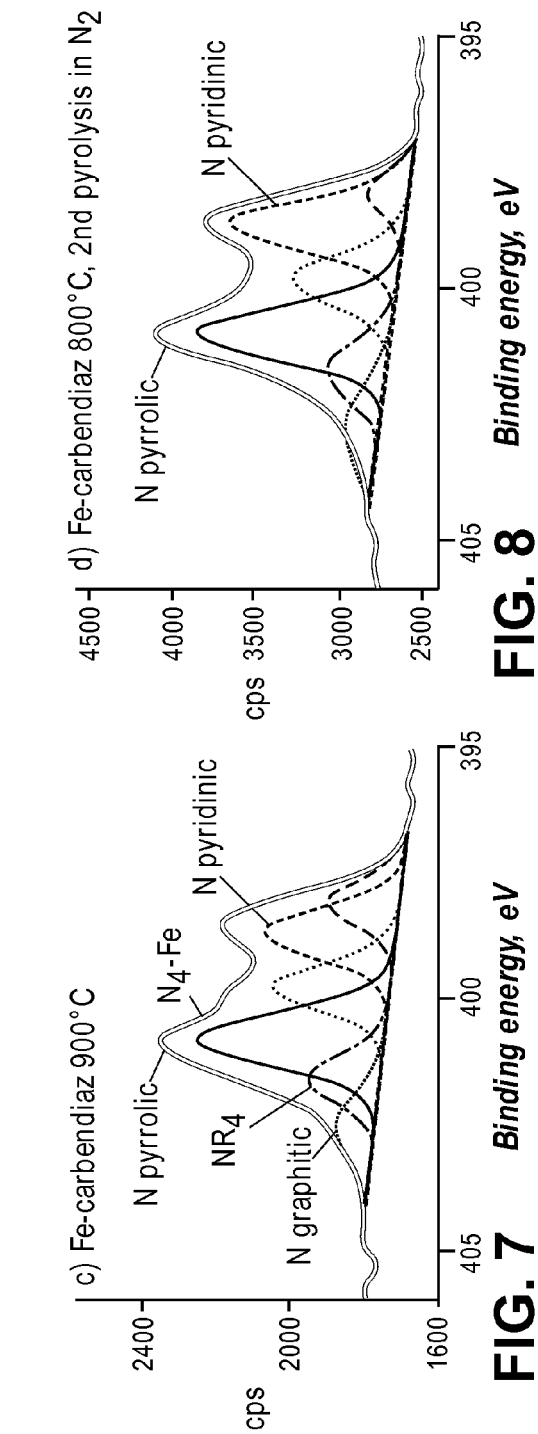

CARBENDAZIM-BASED CATALYTIC MATERIALS

CROSS-REFERENCE TO RELATED APPLICATIONS

The following application claims benefit of U.S. Provisional Application No. 61/593,542 which is hereby incorporated by reference in its entirety.

BACKGROUND

Fuel cells are receiving increasing attention as a viable energy-alternative. In general, fuel cells convert electrochemical energy into electrical energy in an environmentally clean and efficient manner. Fuel cells are contemplated as potential energy sources for everything from small electronics to cars and homes. In order to meet different energy requirements, there are a number of different types of fuel cells in existence today, each with varying chemistries, requirements, and uses.

As one example, Direct Methanol Fuel Cells (DMFCs) rely upon the oxidation of methanol on an electrocatalyst layer to form carbon dioxide. Water is consumed at the anode and produced at the cathode. Positive ions (H+) are transported across a proton exchange membrane to the cathode where they react with oxygen to produce water. Electrons can then be transported via an external circuit from anode to cathode providing power to external sources.

As another example, polymer electrolyte membrane (PEM) fuel cells (also called proton exchange membrane fuel cells) use pure hydrogen (typically supplied by a hydrogen tank) as a fuel. A stream of hydrogen is delivered to the anode side of a membrane-electrode assembly (MEA), where it is catalytically split into protons and electrons. As with the DMFC, the positive ions are transported across a proton exchange membrane to the cathode where they react with oxygen to produce water.

Currently, one of the limiting factors in the wide scale commercialization of PEM and DMFC fuel cells is the cost associated with precious metals. Both DMFC and PEM fuel cells commonly use platinum as an electrocatalyst. Nobel metals such as platinum are needed to catalyze the sluggish oxygen reduction reaction (ORR) at the cathode. One of the major routes to overcome this limitation is to increase the platinum utilization in noble-metal based electrocatalysts. Another viable route is to use a less expensive, yet still sufficiently active catalyst in larger quantities. Several classes of non-platinum electrocatalysts have been identified as having adequate oxygen reduction activity to be considered as potential electrocatalysts in commercial fuel cell applications.

Generally, known non-platinum electrocatalysts are supported on high surface area carbon blacks. This is done to increase dispersion, active surface area, and conductivity of the catalytic layer. The synthesis procedure usually includes precipitation of the precursor molecules onto the supporting substrate and pyrolyzation of the supported precursor.

Metal-Nitrogen-Carbon (M-N—C) catalysts have been found to be very promising for electrochemical oxygen reduction applications in fuel cell membrane electrode assemblies (MEAs), stacks and fuel cell systems. Critical aspects of the materials include the presence of metallic particles, conjugated carbon-nitrogen-oxide-metallic networks, and nitrogen-bonded carbon. The metallic phase includes metallic, oxide, carbide, nitride, and mixtures of these states. The chemical states and bonding of the N/C/M networks and N/C networks influences performance, for example, increased overall nitrogen content improves ORR performance. However, these systems still suffer from several significant drawbacks including: low stability in acidic environments, low durability in acid and alkaline environments, high costs of nitrogen precursors and low activity in ORR compared with platinum. The problem of low stability in acid is connected to leaching of metal from carbon-nitrogen network. Low durability in acid and alkaline solutions is explained by the evolution of significant amount of $H_2O_2$ in these environments which is corrosive for both metal and carbon-nitrogen networks. The low activity is possibly due to the low metal loading, and as a result in low concentration of active sites in such catalysts due to using external carbon source (high surface carbons like Vulcan, KetjenBlack etc).

SUMMARY

In the present disclosure a method of preparation of carbendazim (M-CBDZ)-based catalytic materials utilizing a sacrificial support approach and using inexpensive and readily available precursors is described.

BRIEF DESCRIPTION OF THE DRAWINGS

FIG. 5 shows high resolution N 1 s spectra for pyrolyzed CBDZ.
FIG. 6 shows high resolution N 1 s spectra for Fe-2CBDZ pyrolyzed at 800° C.
FIG. 7 shows high resolution N 1 s spectra for Fe-CBDZ pyrolyzed at 900° C.
FIG. 8 shows high resolution N 1 s spectra for Fe-CBDZ which has undergone a second pyrolyzation step in an ammonia atmosphere.

DETAILED DESCRIPTION

Figure 1:
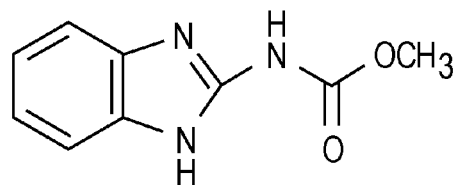
FIG. 1 is the chemical formula of carbendazim.

According to an embodiment, the present disclosure provides novel catalysts and catalytic materials and methods for making the same. In contrast to many previously described methods of producing M-N—C-based catalytic materials, which utilize starting materials that are known to complex with iron and/or which are chelate-like in structure, the present disclosure utilizes a precursor, carbendazim (CBDZ) which does not normally form complexes with iron and which has a non-chelate structure. The chemical structure of carbendazim is shown in FIG. 1. Carbendazim is best known as a broad spectrum benzimidazole carbonate fungicide. However, in the present disclosure, carbendazim is used as a carbon precursor in the formation of a novel highly active non-PGM catalyst for oxidation reduction reactions.

For the sake of clarity, in the present application the term "catalyst" is used to refer to a final product, suitable for use, for example, in a fuel cell, which has catalytic activity. The catalyst may include multiple types of materials, some of which may not in themselves have catalytic activity (for example, supporting material.) The term "catalytic material" is any material which has catalytic activity either on its own or as part of a catalyst.

The present disclosure provides both one-step and two-step synthesis methods for the carbendazim-based catalytic materials described herein. Both steps rely on the introduction of carbendazim onto a sacrificial support and pyrolysis of the resulting material.

According to a more specific one-step example, a catalytic material according to the present disclosure may be synthesized by infusing a sacrificial support with carbendazim and, if desired, metal precursors. The ratio of metal to carbendazim before synthesis may be any desirable ratio. According to various specific examples, a catalytic material may be formed wherein the metal is Iron and having a Fe to carbendezim ratio (Fe:CBDZ) of between 1:4 and 1:12, more specifically between 1:6 and 1:10, and more specifically of 1:8.

It will be appreciated that the sacrificial support may be synthesized and infused in a single synthesis step or the sacrificial support may be synthesized first (or otherwise obtained) and then infused with carbendazim and the appropriate metal precursors. The infused sacrificial support is then subjected to heat treatment, (such as pyrolysis) in an inert ($N_2$, Ar, He, etc.) or reactive ($NH_3$, acetonitrile, etc.) atmosphere.

According to one embodiment, the sacrificial support is infused with carbendazim and iron precursors. Suitable iron precursors include, but are not limited to, iron nitrate, iron sulfate, iron acetate, iron chloride, etc. Furthermore, it will be appreciated that other transition metals such as Ce, Cr, Cu Mo, Ni, Ru, Ta, Ti, V, W, and Zr can be substituted in place of iron, by simply using precursors of those metals instead. Examplary transition metal precursors include, but are not limited to cerium nitrate, chromium nitrate, copper nitrate, ammonium molybdate, nickel nitrate, ruthenium chloride, tantalum isopropoxide, titanium ethoxide, vanadium sulfate, ammonium tunstanate and zirconium nitrate. Furthermore, according to some embodiments the presently described methodologies may utilize precursors of two or more metals to produce multi-metallic catalysts.

Of course it will be appreciated that given the high temperatures that the sacrificial support will be subjected to during the synthesis method, it is important to select a sacrificial support which is non-reactive to the catalytic materials under the specific synthesis conditions used. Accordingly, it will be appreciated that silica is a preferred material for the sacrificial support, but that other suitable materials may be used. Other suitable sacrificial supports include, but are not limited to zeolites, aluminas, and the like. The support may take the form of spheres, particles, or other two or three dimensional regular, irregular, or amorphous shapes. The spheres, particles, or other shapes may be monodisperse, or irregularly sized. The spheres, particles, or other shapes may or may not have pores and such pores may be of the same or different sizes and shapes.

It should be appreciated that the size and shape of the silica particles may be selected according to the desired shape(s) and size(s) of the voids within the electrocatalyst material. Accordingly, by selecting the particular size and shape of silica particles, one can produce an electrocatalyst having voids of a predictable size and shape. For example, if the silica particles are spheres, the electrocatalyst will contain a plurality of spherical voids. Those of skill in the art will be familiar with the electrocatalyst Pt—Ru black, which consists of a plurality of platinum-ruthenium alloy spheres. An electrocatalyst formed from using silica spheres with the above-described method looks like a negative image of the Pt—Ru black; the space that existed as a void in the Pt—Ru black is filled with metal electrocatalyst, and the space that existed as metal electrocatalyst in the Pt—Ru black is void.

As stated above, according to some embodiments, silica spheres of any diameter may be used. In some preferred embodiments, silica particles having a characteristic length of between 1 nm and 100 nm, in more preferred embodiments, silica particles having characteristic lengths of between 100 nm and 1000 nm may be used and in other preferred embodiments, silica particles having characteristic lengths of between 1 mm and 10 mm may be used. Further mesoporous silica can also be used in the templating synthesis approach. In this case the templating involves intercalating the mesopores of the material and results in a self-supported electrocatalysts with porosity in the 2-20 nm range. In one particular embodiment, the silica template is Cabosil amorphous fumed silica (325 $m^2/g$). As stated above, because the spheres serve as the template for the formation of the electrocatalyst, in an embodiment where silica particles having an average diameter of 20 nm is used, the spherical voids in the electrocatalyst will typically have a diameter of approximately 20 nm. Those of skill in the art will be familiar with a variety of silica particles that are commercially available, and such particles may be used. Alternatively, known methods of forming silica particles may be employed in order to obtain particles of the desired shape and/or size.

As stated above, after deposition and/or impregnation of the carbendazim and metal precursors on the sacrificial support, the material is heat treated either in an inert atmosphere such as $N_2$, Ar, or He, or in a reactive atmosphere such as $NH_3$ or acetonitrile. Inert atmospheres are typically used when the infused materials are nitrogen rich, as the inert atmosphere enables the production of a high number of active sites with Fe (or other metal) N4 centers. However, it may be desired to use a nitrogen rich atmosphere if infused material is rich in carbon and depleted in nitrogen, as the nitrogen rich atmosphere will enable production of the Fe (or other metal) N4 centers. As described in greater detail in the experimental section below, according to some preferred embodiments, the materials of the present are subjected to heat treatment in a reactive atmosphere.

According to some embodiments, particularly embodiments wherein a single step synthesis method is used, optimal temperatures for heat treatment are typically between 500° C. and 1100° C. According to some embodiments, heat treatment may preferably be between 750° C. and 900° C., or more preferably between 775° C. and 825° C. In some embodiments, heat treatment of around 800° C. is preferred, as our experimental data showed this temperature to produce catalysts having a high amount of catalytic activity for certain specific materials (see experimental section below).

After heat treatment, the sacrificial support is removed using suitable means. For example, the sacrificial support may be removed via chemical etching. Examples of suitable etchants include NaOH, KOH, and HF. According to some embodiments, it may be preferable to use KOH, as it preserves all metal and metal oxide in the catalyst and, if the species are catalytically active, use of KOH may, in fact, increase catalytic activity. Alternatively, in some embodiments, HF may be preferred as it is very aggressive and can be used to remove some poisonous species from the surface of the catalyst. Accordingly, those of skill in the art will be able to select the desired etchants based on the particular requirements of the specific catalytic material being formed.

As stated above, the presently described catalytic materials can also be synthesized using a two-step procedure. In this procedure, the carbendazim and metal precursors are infused in the sacrificial support, which is then subjected to a first heat treatment step, such as pyrolysis in order to produce an intermediate material that is rich with unreacted iron. The intermediate material is then subjected to a second heat treatment step, which may be, for example, a second pyrolysis treatment, resulting in newly formed active sites. After the second heat treatment, the sacrificial support is removed using chemical etching or other suitable means as described above.

In embodiments utilizing a two-step procedure, and therefore, two separate heat treatment steps, it may desirable for the different heat treatment steps to be conducted under different conditions, for example at different temperatures and/or for different durations of time. For example, the first heat treatment step may be performed at a higher temperature, such as 800° C. for 1 hr and the second heat treatment step may be performed at a temperature between 800 and 1000° C. for a period of time between 10 minutes and 1 hour.

As described in greater detail in the examples section below, in contrast to conventional synthesis methods, the sacrificial support-based method described herein circumvents the use of carbon supports, resulting in higher surface area and 3D porous structure. According to some embodiments, the catalytic material formed during the thermal decomposition of the Fe-CBDZ composite material comprises substantial amounts (i.e. greater than 75%) of carbon derived from carbendazim. Accordingly, greater than 75%, 80%, 85%, 90%, 95%, 99%, of the carbon in the composite material may be derived from CBDZ. According to some embodiments, all (100%) of the carbon in the composite material is derived from carbendazim. Ultimately, the formed catalytic material is self-supported after the sacrificial support is removed, and it possesses a high density of active sites.

It will be appreciated that some in some applications a mono-metallic catalyst may not be sufficiently stable or active to replace traditional platinum- or platinum alloy-based catalysts. Accordingly, as indicated above, according to some embodiments, the presently described method may incorporate the use of precursors of multiple metals in order to achieve a desired stability and/or activity.

According to some embodiments, it may be desirable to produce large amounts of the catalysts described herein, for example in a batch-wise process. Accordingly, the present disclosure further provides a method for large-scale preparation of the presently described catalysts. According to an embodiment, the present disclosure provides a method which combines a sacrificial support-based methodology with spray pyrolysis to produce self-supported catalysts. According to this method, the spray pyrolysis method is a continuous method while the sacrificial support-based methodology is performed batch-wise. According to an exemplary method, the carbendazim and metal precursor materials described herein are mixed with a silica support, atomized, and dried in a tube furnace. The powder obtained from this procedure is then collected on a filter. The collected powder is then heat treated. Finally, the sacrificial support is removed, for example by leaching with HF or KOH.

It will be appreciated that the above-described large-scale production method is suitable for use for a wide variety of precursors and materials and thus not necessarily limited to the catalysts disclosed herein.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a catalyst" includes a plurality of such catalysts, and so forth.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

All patents and publications referenced below and/or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

Additional information may be gathered from the Examples section below. The reaction tests shown and described in the drawings and in the following examples clearly demonstrate that catalysts prepared using the method described possess high Oxygen Reduction activity in acid media. Further, the mechanism of oxygen reduction shows the direct reduction of oxygen to water by a 4 electron pathway, preventing corrosive peroxide production and therefore improving stability and durability of catalysts. Thus, catalysts of the composition and using the preparation method described herein, including but not limited to the described materials shown herein, are effective catalysts for oxygen reduction.

EXAMPLES

1. Fe-CBZD Catalyst Synthesis

Fe-CBDZ catalysts were prepared by a sacrificial support method. First, a calculated amount of silica (Cab-O-Sil® L90, surface area 90 m$^2$ g$^{-1}$) was dispersed in water in an ultrasound bath. Then, a suspension of carbendazim (Carbendazim, Sigma-Aldrich) in water was added to the silica and ultrasonicated for 20 minutes. Finally, a solution of iron nitrate (Fe(NO$_3$)$_3$*9H$_2$O, Sigma-Aldrich) was added to SiO$_2$-CBDZ solution and ultrasonicated for 8 hours (the total metal loading on silica was calculated as ~15 wt. %). After ultrasonication, the viscous solution of silica and Fe-CBDZ was dried overnight at T=85° C. The resulting solid material was ground to a fine powder in an agate mortar, and then subjected to heat treatment (HT). The general conditions of HT were UHP nitrogen (flow rate 100 cc min$^{-1}$), 20 deg min$^{-1}$ temperature ramp rate, and a 1.5 hour pyrolyzation time. The experimental variable component of HT temperatures was of 750° C., 800° C., 850° C. and 900° C. After heat treatment silica was leached by means of 25 wt. % HF overnight. Finally the Fe-CBDZ material was washed with DI water until neutral pH was achieved and then dried at T=85° C. A second heat treatment was performed in ammonia atmosphere at T=950° C. for 30 minutes in inert (N$_2$) or reactive (NH$_3$) atmospheres. In order to evaluate the influence of a second heat treatment on catalytic activity, best performed material was heat treated at T=950° C. in inert (N$_2$) or reactive (NH$_3$) atmospheres. The same synthesis method was performed with carbendazim only to enable the comparison of the activity of no-iron added carbendazim with iron-contained materials.

In the experiments where variations of Fe:CBDZ mass ratio were compared, the catalysts synthesized were: no-iron added, Fe-4CBDZ, Fe-6CBDZ, Fe-8CBDZ, Fe-10CBDZ and Fe-12CBDZ.

In the experiments where variations of Fe:CBDZ mass ratio were compared, the catalysts synthesized were: no-iron added, Fe-4CBDZ, Fe-6CBDZ, Fe-8CBDZ, Fe-10CBDZ and Fe-12CBDZ. The ratio of Fe:CBDZ as used herein refers to the initial mixture of iron nitrate with carbendazim before heat treatment in amounts: 1 g of Fe(NO$_3$)$_3$ to 4 g of CBDZ, 1 g of Fe(NO$_3$)$_3$ to 6 g of CBDZ, 1 g of Fe(NO$_3$)$_3$ to 8 g of CBDZ, 1 g of Fe(NO$_3$)$_3$ to 10 g of CBDZ and 1 g of Fe(NO$_3$)$_3$ to 12 g of CBDZ.

2. Ring Disk Electrode

Electrochemical analysis for synthesized catalysts was performed using the Pine Instrument Company electrochemical analysis system. The rotational speed reported was 1200 RPM, with a scan rate of 5 mV sec$^{-1}$. The electrolyte was 0.5 M H$_2$SO$_4$ saturated in O$_2$ at room temperature. A platinum wire counter electrode and an Ag/AgCl reference electrode were used.

Working electrodes were prepared by mixing 5 mg of the Fe-CBDZ electrocatalyst with 850 μL, of isopropyl alcohol, and 150 μL, of Nafion® polymer (0.5% wt., DuPont). The mixture was sonicated before 30 μL, was applied onto a glassy carbon disk with a sectional area of 0.2474 cm2. The loading of catalyst on the electrode was 0.6 mg cm-2.

3. DoE Durability Protocol for Non-PGM Cathode Catalysts

The working electrode was prepared as mentioned above with reduced catalyst loading (0.2 mg cm$^{-2}$). Electrolyte was 0.1M H$_2$SO$_4$ saturated with O$_2$. Durability tests were performed at rotation rate of 900 RPM with scan rate 50 mV s$^{-1}$. Potential range was selected according the recommendations of the DoE of 0.2-1.1V vs. RHE.

4. MEA Fabrication and Tests

Inks for MEA were prepared by mixing of 75 mg of catalyst with 1.2 g of 5 wt % Nafion® polymer solution and 3.5 ml of IPA (nominal content of solid Nafion® polymer was 45 wt %). Mixture was sonicated at ultrasound bath for 2 hours. A hand spray technique was used to deposit 4 mg cm$^{-2}$ catalyst onto the surface of 5 cm$^2$ SGL 25BC carbon paper. The MEA was assembled by hot pressing the anode (Pt/C JM 0.5 mg cm-2), membrane (Nafion® N211 polymer) and hand-sprayed cathode at T=135° C., t=3 minutes and pressure 1000 lbs.

Test conditions were selected as: O$_2$/H$_2$ Tcell=80° C., 100% RH, flow rates for anode and cathode 100 ccm.

5. Result and Discussion

Figure 2:
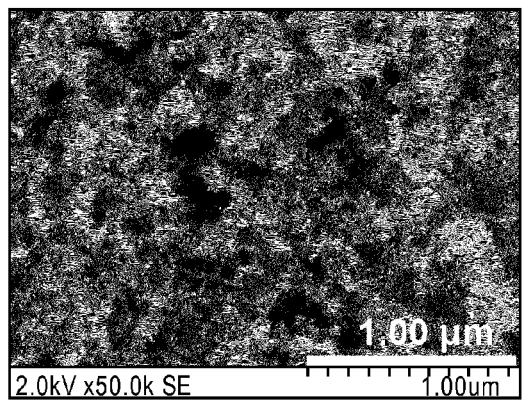
FIG. 2 is an SEM image of a CBDZ catalyst with no iron.
Figure 3:
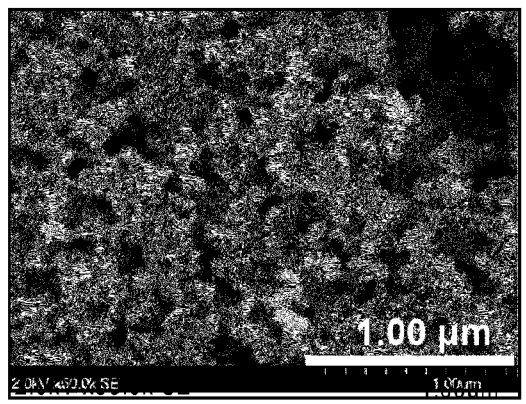
FIG. 3 is an SEM image of an Fe-4CBDZ catalyst.
Figure 4:
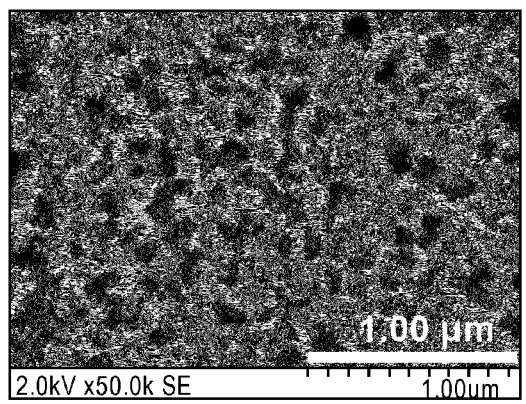
FIG. 4 is an SEM image of an Fe-12CBDZ catalyst.

Morphological analysis of the carbendazim, and Fe-CBDZ materials synthesized with different Fe:CBDZ mass ratio shows that all materials possesses a well-developed porous structure (FIGS. 2-4). Large pores were formed during leaching of agglomerated silica, whereas small pores were formed after removal of individual SiO$_2$ particles (~30 nm). The surface area of all materials was similar (~600 m$^2$ g$^{-1}$). As it can be seen by comparing FIGS. 2-4, an increase of carbendazim concentration does not affect morphology.

Figure 9:
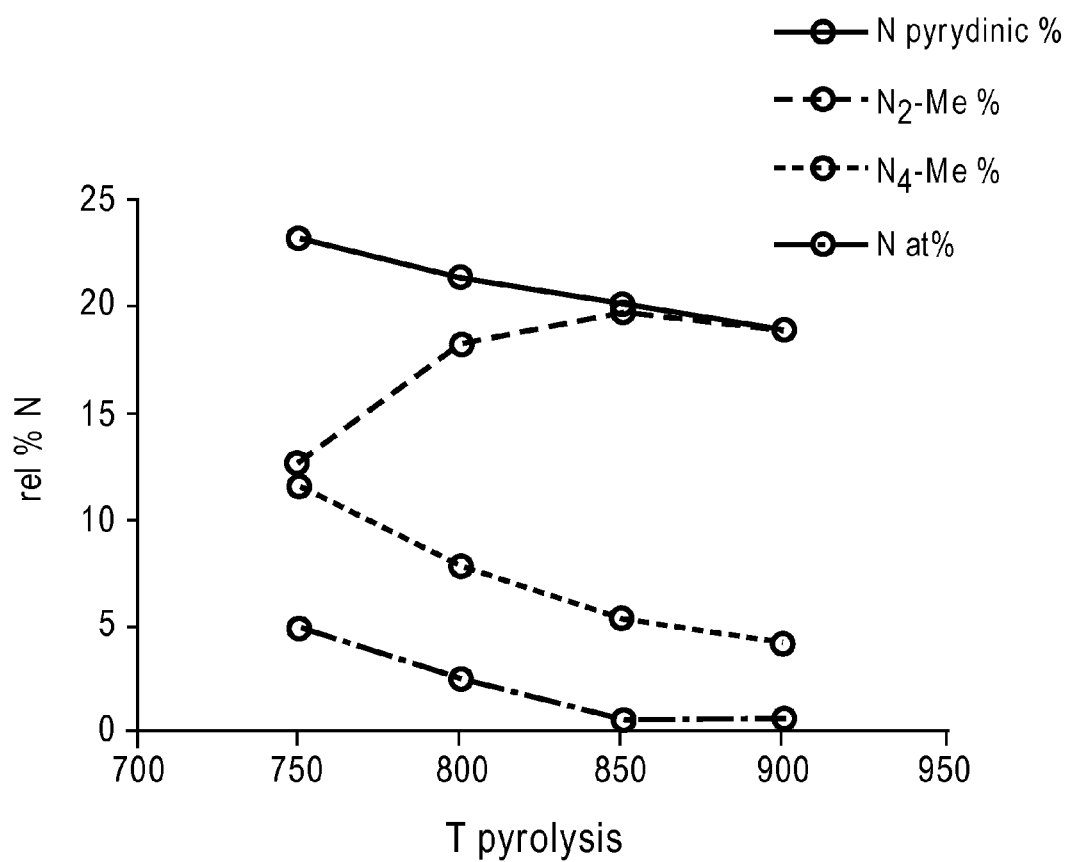
FIG. 9 is a graph showing the change in at % of N and relative % of different N species as a function of T of pyrolysis.

XPS analysis revealed that materials mainly consist of carbon with several atomic percents of nitrogen and oxygen. Iron content was determined as 0.1-0.3 at % due to the dissolution of unreacted iron in HF. FIGS. 5-8 show N is curve fit results for a subset of samples. The largest peak in the metal-free sample is pyrrolic N at 400.7 eV. Significant amounts of nitrile (398 eV), pyridinic (398.6 eV) and amine (399.6 eV) with small amounts of quaternary (401.8 eV) and graphitic (403 eV) nitrogen are also present. It has been previously shown that pyrrolic nitrogen is the main type of nitrogen responsible for the first 2e-step of O$_2$ to H$_2$O$_2$ reduction. In addition to all these peaks, spectra for all samples containing Fe were curve fitted using two peaks due to N-metal coordination. The first is Fe—N$_2$ which was constrained to have a shift of +0.8 eV from pyridinic nitrogen (399.4 eV) and the other type is Fe—N$_4$ shifted 1.1 eV from pyridinic (399.7 eV). The latter is the exact position of amine groups in the metal-free sample. FIG. 9 follows the evolution of the above-mentioned species as a function of pyrolysis temperature. It can be seen that the total amount of nitrogen decreases significantly. Most of the Fe—N$_2$ centers disappear with a higher pyrolysis temperature. Pyridinic nitrogen decreases as well while the amount of Fe—$N_4$ centers increases and reaches a maximum at a pyrolysis temperature of 850° C. While not shown, it was also observed that quaternary nitrogen disappears at higher temperatures, while graphitic nitrogen increases.

Figure 10:
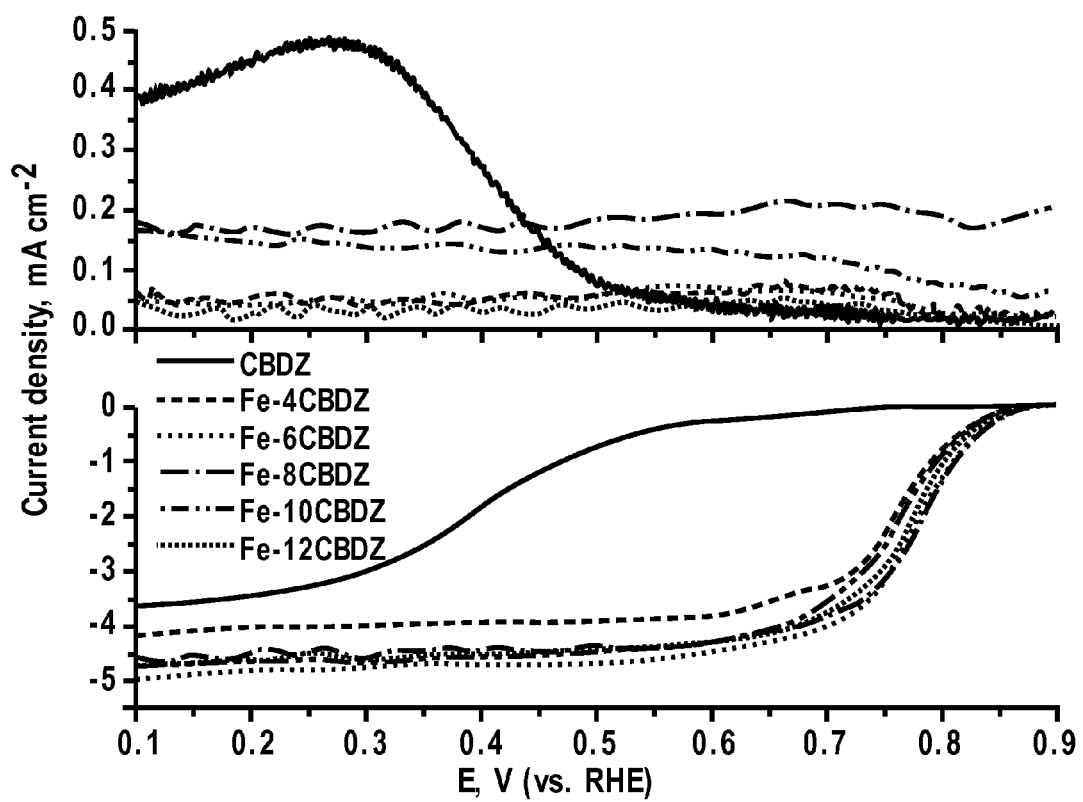
FIG. 10 shows RRDE data for Fe-CBDZ catalysts with variation of Fe:CBDZ ratio: CBDZ (———), Fe-4CBDZ (— —), Fe-6CBDZ ( . . . ), Fe-8CBDZ (—.—), Fe-10CBDZ (—..—) and Fe-12CBDZ ( . . . . ). Conditions: 0.5M H2SO4 saturated with O2, 1200 RPM, 5 mV s-1, catalyst loading 0.6 mg cm-2.

We have previously shown on two classes of N—C precursors (4amino-antipyrine and polyethyleneimine) that heat treated metal-free materials possess extremely low activity and produce substation amount of $H_2O_2$, which indicates utilization of the 2e-mechanism. (See e.g., A. Serov, M. H. Robson, K. Artyushkova, P. Atanassov "Templated non-PGM cathode catalysts derived from iron and poly(ethyleneimine) precursors" Appl. Catal. B 127 (2012) 300-306 and A. Serov, M. H. Robson, B. Halevi, K. Artyushkova, P. Atanassov "Highly Active and Durable Templated Non-PGM Cathode Catalysts Derived from Iron and Aminoantipyrine" Electrochem. Comm 22 (2012) 53-56, hereby incorporated by reference.) The optimization of Fe:CBDZ ratio and the influence of carbendazim concentration on ORR activity is shown FIG. 10. It was confirmed that the iron-free CBDZ-based material had a significantly lower ORR performance and produced ~8 times more peroxide compared to the Fe-CBDZ materials. As shown, the Fe-CBDZ material having a mass ratio of Fe:CBDZ=1:8 demonstrated the best performance and that ratio was selected for further experiments.

Figure 11:
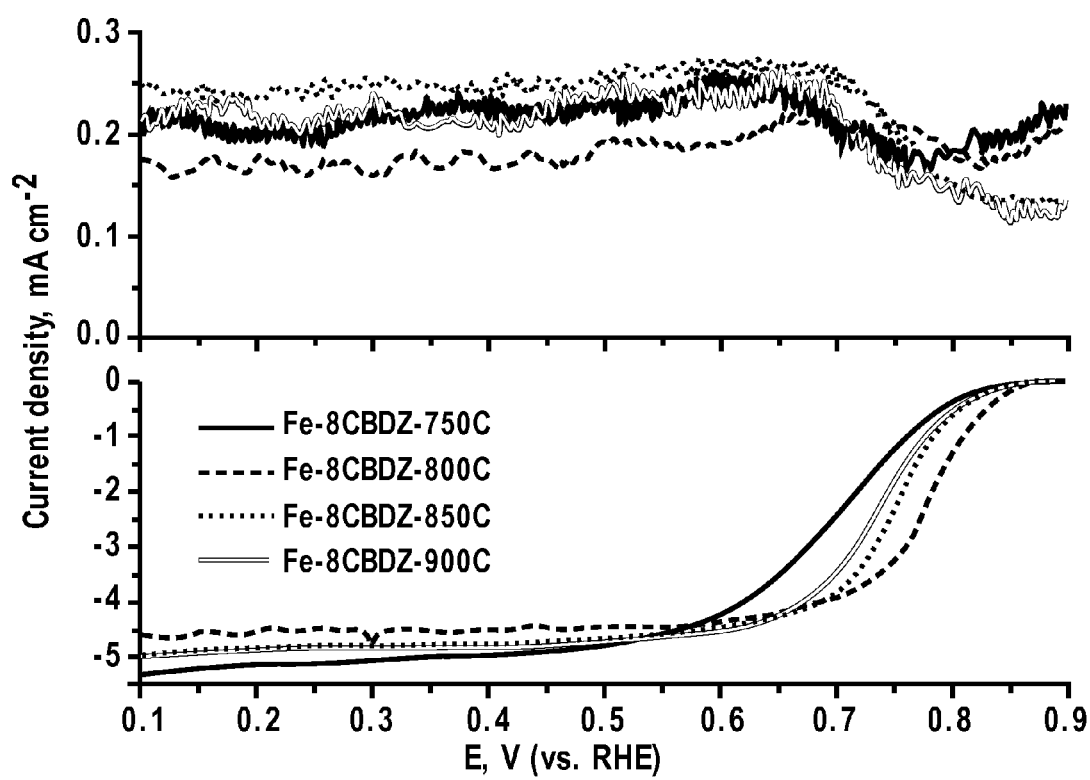
FIG. 11 shows RRDE data for Fe-8CBDZ catalysts heat treated at different temperatures: T=750° C. (———), T=800° C. (— —), T=850° C. ( . . . ) and T=900° C. (=). Conditions: 0.5M H2SO4 saturated with O2, 1200 RPM, 5 mV s-1, catalyst loading 0.6 mg cm-2.

It has previously been determined [1, 33-36, 38] that heat treatment parameters have a crucial affect on catalytic activity. (See e.g., F. Jaouen, E. Proietti, M. Lefèvre, R. Chenitz, J.-P. Dodelet, G. Wu, H. T. Chung, C. M. Johnston, P. Zelenay Energy Environ. Sci. 4 (2011) 114-130; M. H. Robson, A. Serov, K. Artyushkova, P. Atanassov "A Mechanistic Study of 4-Aminoantipyrine and Iron Derived Non-Platinum Group Metal Catalyst on the Oxygen Reduction Reaction" Electrochim Acta, 90 (2013) 656-665; S. Brocato, A. Serov, P. Atanassov "pH Dependence of Catalytic Activity for ORR of the non-PGM Catalyst Derived from Heat-Treated Fe-Phenanthroline" Electrochim Acta, 87 (2013) 361-365; A. Serov, M. H. Robson, K. Artyushkova, P. Atanassov "Templated non-PGM cathode catalysts derived from iron and poly(ethyleneimine) precursors" Appl. Catal. B 127 (2012) 300-306; A. Serov, M. H. Robson, M. Smolnik, P. Atanassov "Templated bi-metallic non-PGM catalysts for oxygen reduction" Electrochim Acta 80 (2012) 213-218; and A. Serov, M. H. Robson, B. Halevi, K. Artyushkova, P. Atanassov "Highly Active and Durable Templated Non-PGM Cathode Catalysts Derived from Iron and Aminoantipyrine" Electrochem. Comm 22 (2012) 53-56, each of which is hereby incorporated by reference). The series of Fe-CBDZ catalyst were prepared with variation of heat treatment temperature in the range 750-900° C. (FIG. 11). It was found that catalyst prepared at T=800° C. possessed the highest ORR activity. The lowest activity was observed for Fe-CBDZ treated at T=750° C. and despite the fact that the amount of nitrogen is highest at this temperature (FIG. 9) it is obviously what this temperature is sufficient for the formation of active sites. However, we have previously shown that too high a pyrolysis temperature results in a decrease in activity due to decomposition of active sites (See e.g., A. Serov, M. H. Robson, K. Artyushkova, P. Atanassov "Templated non-PGM cathode catalysts derived from iron and poly(ethyleneimine) precursors" Appl. Catal. B 127 (2012) 300-306 and A. Serov, M. H. Robson, B. Halevi, K. Artyushkova, P. Atanassov "Highly Active and Durable Templated Non-PGM Cathode Catalysts Derived from Iron and Aminoantipyrine" Electrochem. Comm 22 (2012) 53-56) and the same observation was made in the present study (FIG. 11).

Figure 12:
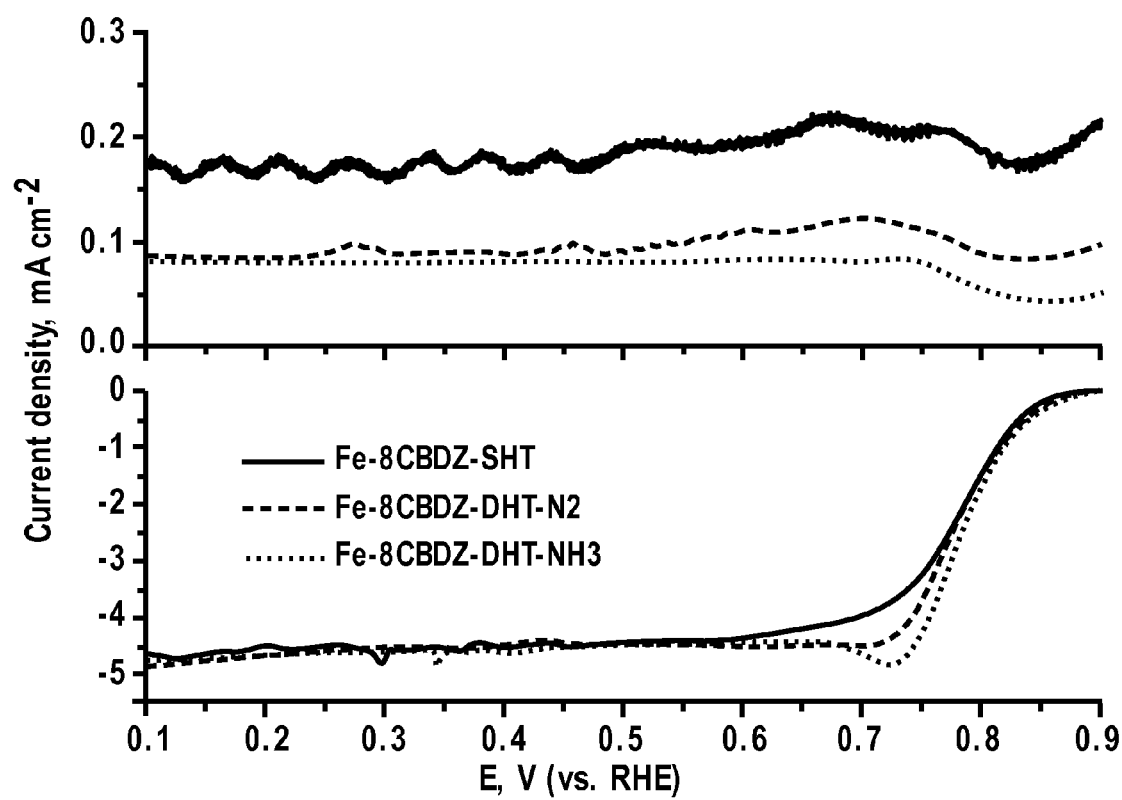
FIG. 12 shows RRDE data for Fe-CBDZ catalysts heat treated second time at different atmospheres: Fe-8CBDZ single heat treated (———), Fe-8CBDZ double heat treated in nitrogen (— —) and Fe-82CBDZ double heat treated in ammonia ( . . . ). Conditions: 0.5M $H_2SO_4$ saturated with O2, 1200 RPM, 5 mV $s^{-1}$, catalyst loading 0.6 mg $cm^{-1}$.

The effect of a second treatment on ORR activity in two different atmospheres: inert (N2) and reactive (NH3) is shown on FIG. 12. Despite the fact that the limiting current was found to be similar for single and double treated materials, it can be seen that that the most increased kinetic activity is found when the second heat treatment is performed in a reactive atmosphere. From this data it can be hypothesized that a second treatment in ammonia increases the amount of active centers associated with Fe—$N_4$.

Figure 13:
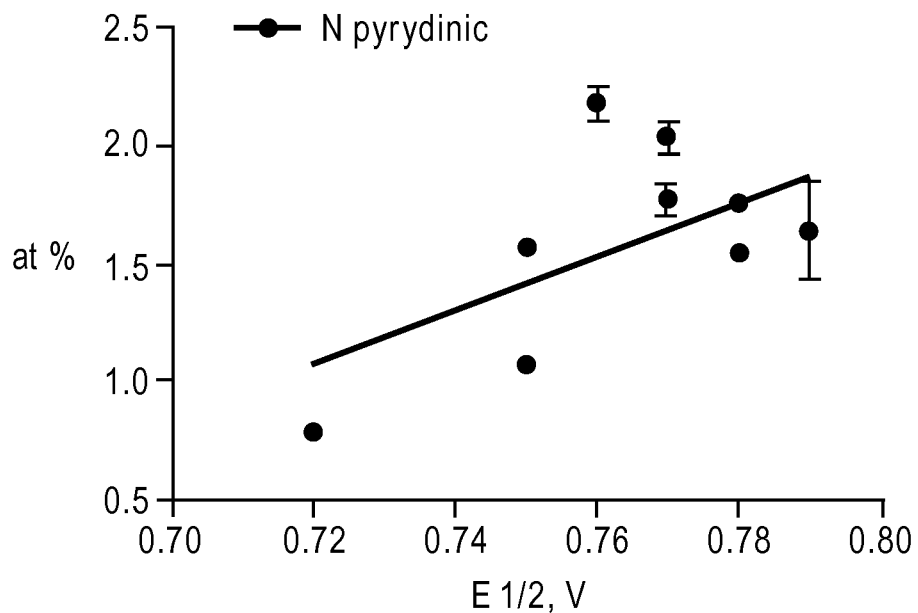
FIG. 13 is a graph showing At % of N pyridinic centers as a function of $E_{1/2}$ for all Fe-CBDZ electrocatalysts.
Figure 14:
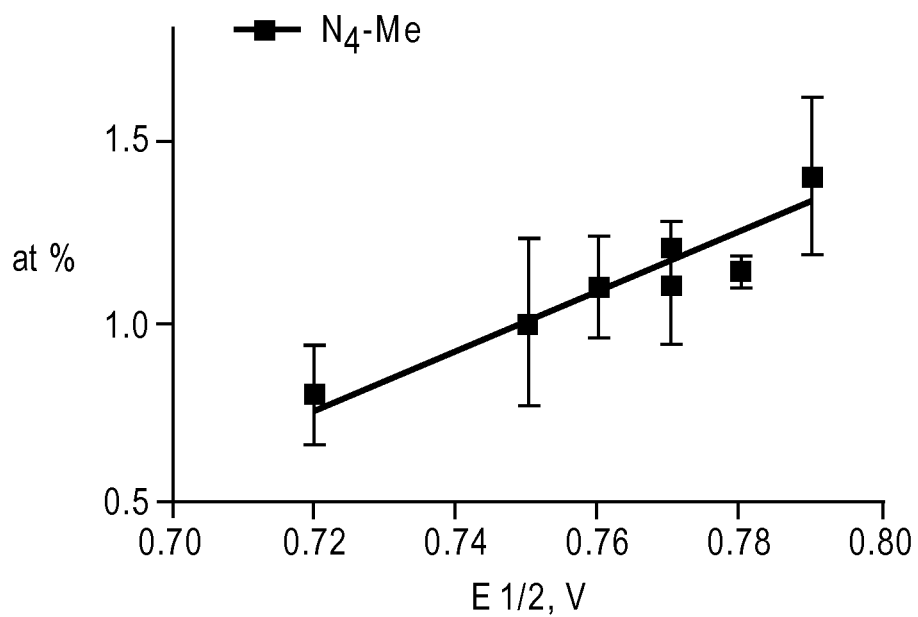
FIG. 14 is a graph showing At % of $N_4$-Fe centers as a function of $E_{1/2}$ for all Fe-CBDZ electrocatalysts.
Figure 15:
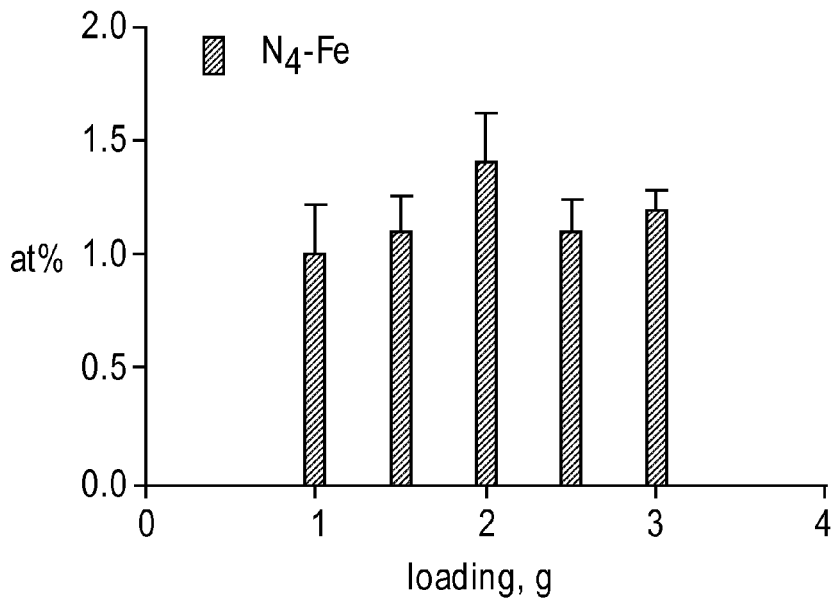
FIG. 15 is a graph showing At % of $N_4$-Fe centers as a function of loading of precursor, all pyrolyzed at 800° C.

An in-depth analysis of the correlation between the surface chemistry of materials (XPS data) and performance (RRDE, E1/2) was then performed. The results are shown in FIGS. 13 and 14. In the figures, the absolute amounts of pyridinic nitrogen and Fe—$N_4$ species as a function of half-way potential E1/2 are plotted. The range of measured E1/2 for samples pyrolyzed at different temperatures and with different ratio of the precursor was 0.72-0.79V. The best activity is observed for Fe-CBDZ samples pyrolyzed at 800° C. There is a clear indication that with an increase in the amount of pyridinic nitrogen, higher electrocatalytic activity towards oxygen reduction is expected, which is in perfect agreement with published data. However, despite the metal-free sample being pyrolyzed at the same conditions, and having significant pyridinic nitrogen content, the metal-free sample shows dramatically lower activity (E1/2=0.40V). This can be explained by the assumption that pyridinic nitrogen centers play a role only in the first 2e-step, which is confirmed by high $H_2O_2$ yield in the iron-free sample. Among the Fe-containing materials, Fe-6CBDZ, Fe-10CBDZ and Fe-12CBDZ have 10-30% larger amounts of pyridinic nitrogen. However, their activity was ~5% worse than that of the best performing Fe-containing material: Fe-8CBDZ. Furthermore, Fe-8CBDZ has the largest amount of Fe—N4 centers (FIG. 15). The presence of Fe bound to N, and particularly in the Fe—$N_4$ configuration, is of critical importance as indicated by very strong correlation (R2=0.9) in FIG. 14). Analysis of correlations between surface moieties and ORR performance indisputably indicates that Fe—$N_4$ is an intrinsic active sites for oxygen reduction in a large number of the Fe—N—C family of catalysts.

Figure 16:
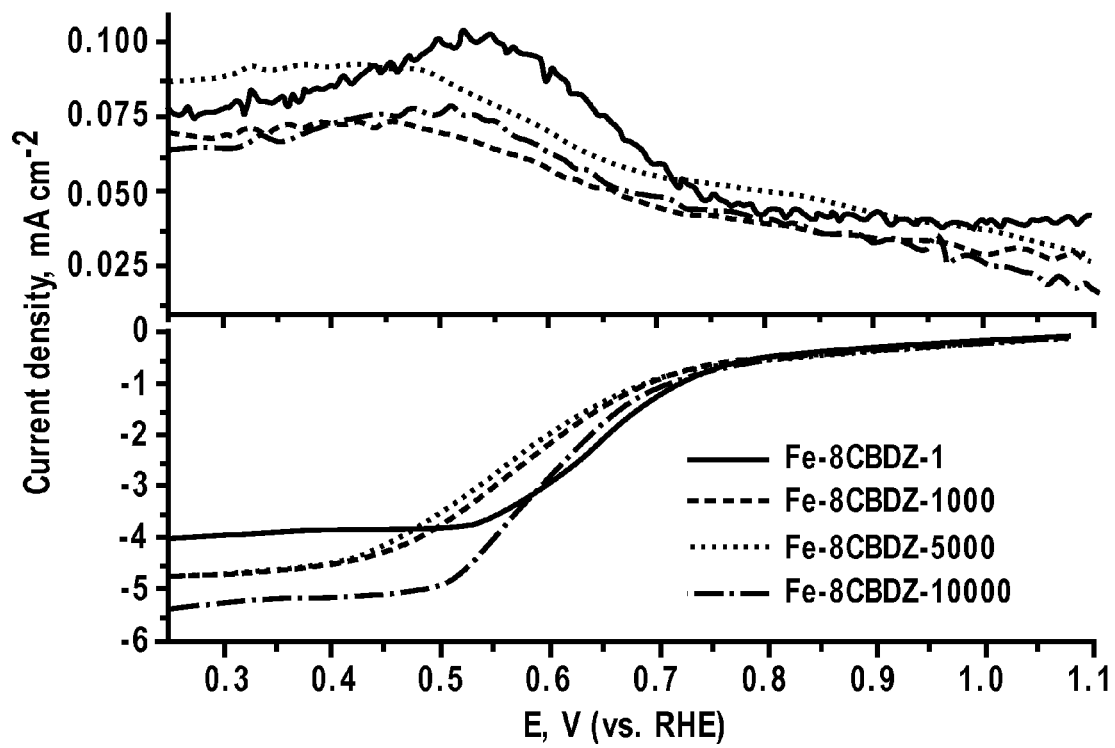
FIG. 16 is a graph of DoE durability data by RRDE method for Fe-8CBDZ, Fe-8CBDZ in BoL (———), Fe-8CBDZ after 1000 cycles (— —), Fe-8CBDZ after 5000 cycles (...), and Fe-8CBDZ after 10000 cycles (— . —). Conditions: 0.1M $H_2SO_4$ saturated with O2, 900 RPM, 50 mV $s^{-1}$, catalyst loading 0.2 mg $cm^{-2}$.

RDE based durability tests were performed under the DoE recommended conditions for non-PGM cathode catalysts. It was found that Fe-8CBDZ is an extremely durable catalyst with a loss of activity after 10000 cycles of just 6% (FIG. 16). The unusual increase in performance between 5000 and 10000 cycles was observed. This unusual increase can be explained by an improvement in accessibility of the active sites to oxygen, most probably due to an increase of hydrophilicity during cycling.

Figure 17:
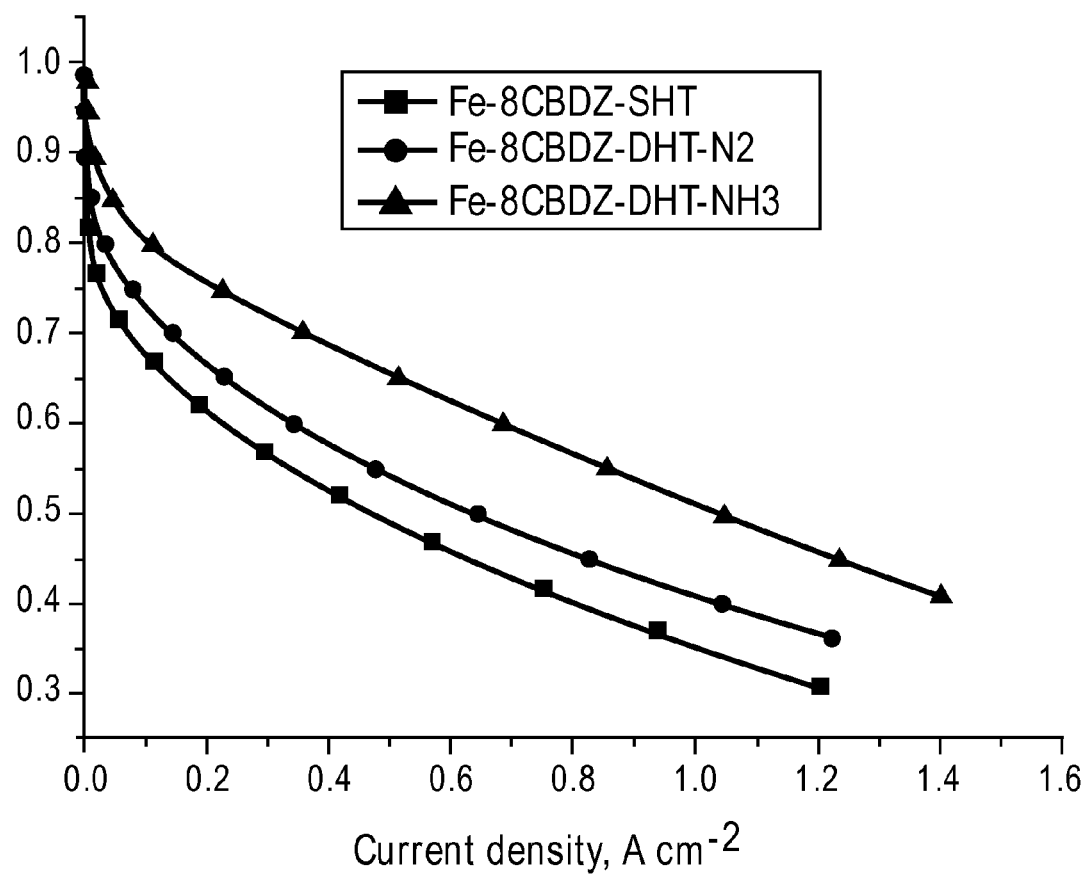
FIG. 17 is a graph showing MEA performance of Fe-8CBDZ catalysts: Fe-8CBDZ single heat treated (■), Fe-8CBDZ double heat treated in $N_2$ (●) and Fe-8CBDZ double heat treated in $NH_3$ (▲). Conditions: 100% RH, O2/H2, anode flow rate: 100 ccm, cathode flow rate: 100 ccm, 30 psig, cell T=80° C.

RRDE data show that Fe-8CBDZ is a very promising material for platinum substitution. In order to prove it, MEA tests were performed for single and double heat treated samples (FIG. 17). The trend in performance was the same as in RRDE experiments: Fe-8CBDZ-DHT-NH3>>Fe-8CBDZ-DHT-N2>Fe-8CBDZ-SHT. Highest activity at 0.6V was found 0.7 A cm-2 which is ~40% of platinum performance. Taking into account the low cost of manufacturing of Fe-CBDZ catalysts and the high activity and durability of this material, it can be considered as a real candidate to replace platinum in oxygen reduction reactions.

What is claimed is:

1. A method for forming a catalytic material comprising:
   providing sacrificial template particles;
   reacting a metal precursor and carbendazim (CBDZ) onto the sacrificial template particles to produce dispersed precursors;
   heat treating the dispersed precursors; and
   removing the sacrificial template particles to produce a highly dispersed, self-supported, high surface area electrocatalytic material.

2. The method of claim 1 wherein the metal precursor is a transition metal precursor.

3. The method of claim 2 wherein the transition metal precursor is iron nitrate.

4. The method of claim 1 wherein heat treating the dispersed precursors comprises pyrolysis.

5. The method of claim 4 wherein pyrolysis is conducted at a temperature above 750° C. and below 900° C.

6. The method of claim 5 wherein pyrolysis is conducted at a temperature between 775 and 825° C.

7. The method of claim 5 wherein pyrolysis is conducted at 800° C.

8. The method of claim 4 wherein pyrolysis is conducted in a reactive atmosphere.

9. The method of claim 8 wherein pyrolysis is conducted in ammonia.

10. The method of claim 1 wherein the ratio of metal precursor:CBDZ prior to heat treatment is between 1:4 and 1:12.

11. The method of claim 10 wherein the ratio of metal precursor:CBDZ prior to heat treatment is between 1:6 and 1:10.

12. The method of claim 11 wherein the ratio of metal precursor:CBDZ prior to heat treatment is 1:8.

13. A catalytic material comprising a metal and a substantial portion of carbon derived from carbendazim (CBDZ).

14. The catalytic material of claim 13 wherein the catalytic material is unsupported.

15. The catalytic material of claim 14 wherein all of the carbon in the material is derived from CBDZ.

16. The catalytic material of claim 13 wherein the metal is derived from a transition metal precursor.

17. The catalytic material of claim 16 wherein the ratio of transition metal precursor:CBDZ is between 1:4 and 1:12.

18. The catalytic material if claim 17 wherein the ratio of transition metal precursor:CBDZ is 1:8.

19. A catalytic material formed by:
   providing sacrificial template particles;
   reacting a metal precursor and carbendazim (CBDZ) onto the sacrificial template particles to produce dispersed precursors;
   heat treating the dispersed precursors; and
   removing the sacrificial template particles to produce a dispersed, self-supported, electrocatalytic material.

20. The catalytic material of claim 19 wherein the dispersed precursors are heat treated by pyrolysis at 800° C. and the ratio of metal precursor:CBDZ prior to heat treatment is 1:8.

* * * * *